United States Patent [19]

Higa et al.

[11] Patent Number: 4,895,854

[45] Date of Patent: * Jan. 23, 1990

[54] ANTITUMOR ALKALOIDS

[75] Inventors: Tatsuo Higa, Okinawa, Japan; Ryuichi Sakai, Vero Beach, Fla.

[73] Assignee: Harbor Branch Oceanographic Institution, Inc., Ft. Pierce, Fla.

[ * ] Notice: The portion of the term of this patent subsequent to Jan. 23, 2007 has been disclaimed.

[21] Appl. No.: 228,868

[22] Filed: Aug. 5, 1988

Related U.S. Application Data

[63] Continuation of Ser. No. 879,094, Jun. 26, 1986, abandoned.

[51] Int. Cl.$^4$ .................. A61K 31/475; C07D 519/00
[52] U.S. Cl. ................................ 514/281; 540/478
[58] Field of Search ..................... 540/478; 514/281

[56] References Cited

U.S. PATENT DOCUMENTS 4,631,149 9/1986 Rinehart, Jr. et al. ............. 540/546

OTHER PUBLICATIONS

Baslow et al., Chemical Abstracts, vol. 73:64847w (1970).
Stempien et al., Chemical Abstracts, vol. 86:95905m (1977).
Ballantine et al., Chemical Abstracts, vol. 87:152455m (1977).
Sakai et al., J. Am. Chem. Soc., vol. 108(20), pp. 6404–6405 (10/01/86).
Nakamura et al., Tetrahedron Letters, vol. 28, No. 6, pp. 621–624 (02/87).

*Primary Examiner*—Diana G. Rivers
*Attorney, Agent, or Firm*—Carroll F. Palmer

[57] ABSTRACT

This invention relates to antitumor alkaloid compositions, a process of producing the compositions and a method for inhibiting tumors utilizing the compositions. More particularly, the compositions are antitumor alkaloids which are derived from marine organisms, i.e., the marine sponge genus Haliclona.

3 Claims, No Drawings

ANTITUMOR ALKALOIDS

FIELD OF THE INVENTION

This invention relates to new cyclic organic compounds which have useful antitumor activity. More particularly, this invention relates to new cyclic alkaloid antitumor compositions derived from marine organisms, i.e., marine sponge, order Haplosclerida, and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Marine organisms and particularly marine sponges are a potential source for chemically and biologically interesting molecules of great diversity. Some such molecules derived from sponges are described in Scheuer, P. J. Ed., *Marine Natural Products, Chemical and Biological Perspectives;* Academic Press; New York, 1978-1983; Vol. I-V; Faulkner, D. J. *Natural Products Reports* 1984, 551-598; Uemura, D.; Takahashi, K.; Yamamoto, T.; Katayama, C; Tanaka, J.; Okumura, Y.; Hirata, Y. *J. Am. Chem. Soc.* 1985, 107, 4796-4798. The entire disclosures of these references are hereby incorporated herein by reference.

Other interesting compositions derived from marine organisms (i.e., caribbean tunicate) and containing a β-Carboline system are described in K. L. Rinehart, Jr., J. Kobayashi, G. C. Harbour, R. G. Hughes, Jr., S. A. Mizsak, T. A. Scahill, *J. American Chemical Society,* 106, 1524 (1984); J. Kobayashi, G. C. Harbour, J. Gilmore and K. L. Rinehart, Jr., ibid. at 1526.

It has now been found that certain cylic alkaloid compositions derived from extracts of the marine sponge, genus, Haliclona, possess useful antitumor activity.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises composition of the general formula (I)

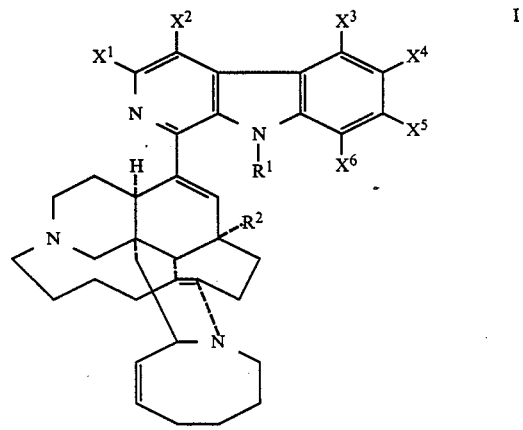

wherein $X^1$, $X^2$, $X^3$, $X^4$, $X^5$, and $X_6$ are hydrogen, halogen, hydroxy, lower alkoxy, lower acyloxy or a lower mono or dialkyl amino group; $R^1$ is hydrogen, lower alkyl, or lower acyl group; $R^2$ is hydrogen, hydroxy, lower alkoxy, or lower acyloxy group.

In other embodiments of the invention the double bonds in the composition of formula I are partially or fully reduced.

In further embodiments of the invention the composition is a mineral or organic acid salt of compositions according to formula I or of compositions according to formula I wherein at least one double bond is reduced.

In preferred embodiments of the invention, the composition is substantially pure. In further preferred embodiments of the invention $R^1$, $R^2$, $X^1$, $X^2$, $X^3$, $X^4$, $X^5$, and $X^6$ are a hydrogen or hydroxy.

In more preferred embodiments of the invention, the invention comprises a composition of the formula (II):

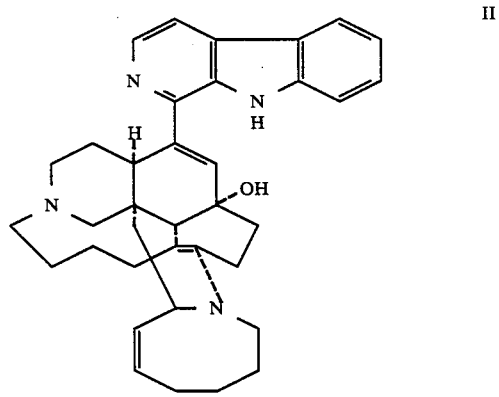

As embodied and fully described herein, the invention also comprises an antitumor composition comprising, as active ingredient, an effective antitumor amount of one or more compositions according to formulae I or II; a composition according to formula I wherein at least one double bond is reduced; or an acid salt of a composition according to formula I or a composition according to formula I wherein at least one double bond is reduced and a non-toxic pharmaceutically acceptable carrier or diluent.

As embodied and fully described herein, the invention also comprises a process to produce the compositions of formulae I and II and their reduced or acid salt derivatives. The process comprises the steps of collecting marine sponge genus Haliclona; contacting the sponge with at least one suitable organic solvent to obtain an extract comprising a composition according to formula I or II or their reduced or acid salt derivatives; and isolating a composition according to formulae I or II or said derivatives from the extract.

In preferred embodiments of the invention the suitable organic solvent is selected from the group consisting of acetone, methyl ethyl ketone, ethyl acetate, methanol, ethanol, and methyl isobutyl ketone.

As embodied and fully described herein, the invention further comprises a method for inhibiting tumors in a host and a therapeutic method for treating cancerous cachexia comprising contacting a tumor with an effective antitumor amount of one or more compositions of formulae I or II or their reduced or acid salt derivatives.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formula (I):

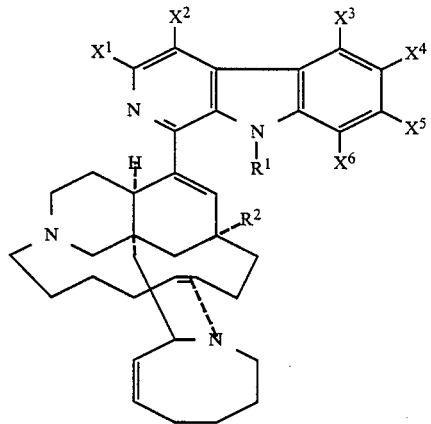

wherein $X^1$, $X^2$, $X^3$, $X^4$, $X^5$, and $X^6$ are a hydrogen, halogen, hydroxy, lower alkoxy, lower acyloxy, or lower mono or dialkyl amino group; $R^1$ is hydrogen, lower alkyl, or lower acyl group; $R^2$ is hydrogen, hydroxy, lower alkoxy, or lower acyloxy group.

In other embodiments of the invention the double bonds in the composition of formula I are partially or fully reduced.

In further embodiments of the invention the composition is a mineral acid (e.g. HCl, $H_2SO_4$, $H_3PO_4$, $HNO_3$, etc.) or organic acid salt of compositions according to formula I or of compositions according to formula I wherein at least one double bond is reduced.

In more preferred embodiments of the invention, the invention comprises compositions of the formula (II):

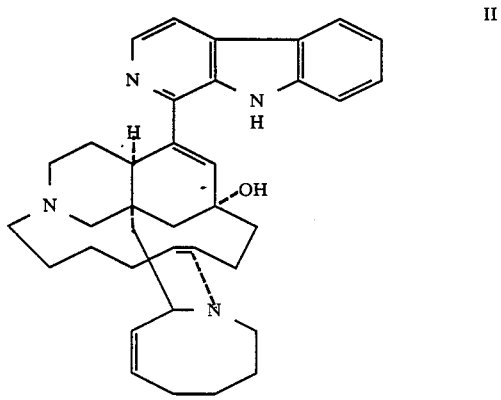

In accordance with the invention, an antitumor composition is provided comprising as active ingredient an effective antitumor amount of one or more of the compositions described above and identified by formulae I or II and their reduced or acid derivatives and a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. The compositions of the invention are active for inhibiting a diverse range of tumors including, but not limited to human lung, colon and mammary tumors such as lung carcinoma A549, ileocecal adenocarcinoma HCT-8, and human breast cancer cells MDAMB. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compositions according to formulae I or II and their reduced or acid derivatives. The effectiveness of the compositions of the invention for inhibiting tumors indicates their usefulness for controlling tumors in hosts including mammals and for treating cancerous cachexia.

In accordance with the invention, a process to produce compositions according to formulae I or II and their reduced or acid salt derivatives comprises the steps of: collecting marine sponge genus Haliclona; contacting the sponge with at least one suitable organic solvent to obtain an organic extract comprising a composition according to formula I or II or their reduced or acid salt derivatives; and isolating a compound according to formulae I or II.

A detailed description and explanation of a preferred embodiment of the process of the invention to produce the compositions according to formula I or II and their reduced or acid salt derivatives is as follows: marine sponge genus Haliclona, is collected by SCUBA at a depth of 30 meters off Munzamo, Okinawa. The marine sponge is contacted with and steeped in acetone as a first solvent for about 48 hours to obtain an extract which is concentrated to yield an aqueous suspension (the water is derived from the natural water content of the sponge). The aqueous suspension is then extracted with ethyl acetate as a second solvent to obtain an extract which comprises a composition according to formula I or II or their reduced or acid salt derivatives. The ethyl acetate extract is concentrated by evaporation to give solid organic residue. The residue is then chromatographed to yield the pure solid product.

While acetone and ethyl acetate are the presently preferred choices for the first and second extracting solvents, respectively, other suitable solvents may be substituted. A suitable solvent should be capable of extracting a compound according to any one of formulae I or II or their reduced or acid salt derivative from other components of the marine sponge. Suitable first and second solvents which may be substituted for either acetone or ethyl acetate include, but are not limited to, the following organic solvents: methyl ethyl ketone; acetone; methanol; ethanol; methyl isobutyl ketone; methylene chloride; chloroform; ether; and tetrahydrofuran.

Any suitable fractionation and isolation techniques may be utilized in accordance with the process of the invention. Suitable fractionation techniques include various chromotography techniques such as, high pressure liquid chromatography (HPLC) with a suitable column as would be known to those skilled in the art including silica gel, Sephadex LH-20; ammonia-treated silica gel; RP-18, RP-8, and LiChrosorb NH2 column. These columns are eluted with suitable eluents such as: heptane; ethyl acetate; methylene chloride; methanol; isopropyl alcohol; and various combinations and ratios thereof as would be known to those skilled in the art. Countercurrent chromatography techniques are also useful for isolating compositions of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLES 1-3

The antitumor cyclic alkaloids of the invention were prepared from a marine sponge, genus Haliclona, according to the following procedures.

EXAMPLE 1

Preparation of Manzamine A

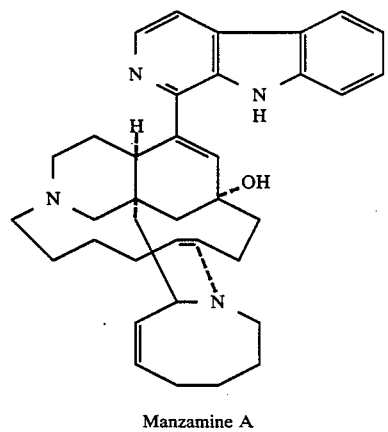

Manzamine A

A sample (880 g wet weight) of marine sponge genus Haliclona was collected off Manzamo, Okinawa in waters at a depth of 30 meters in April 1985. The sponge was extracted by steeping in 1 liter of acetone for 48 hours. After concentration the aqueous suspension was extracted with ethyl acetate (EtOAc) to give 2.3 g of EtOAc soluble residue (solid). A part (1.7 g) of the residue was then chromatographed using in turn columns of silica gel (2:3 heptane-EtOAc), Sephadex LH-20 (1:1 methylene chloride-methanol), ammonia treated silica gel (25:35:1 heptane-EtOAc-isopropanol), LiChrosorb NH2 HPLC column (5:7:0.1 heptane-EtOAc-isopropanol), and finally silica gel treated with pyridine (2:1 methylene chloride-EtOAc) to give 125 mg of solid. Recrystallization from metanol gave 100 mg of pure manzamine A hydrochloride as colorless crystals, mp>240° C. (dec.); $[\alpha]_D^{20}+50°$ (c 0.28, CHCl3); IR (KBr) 3280, 3150, 3050, 3000, 2920, 2800, 2760, 2630, 2560, 1617, 1555, 1488, 1448, 1418, 1385, 1370, 1315, 1270, 1230, 1180, 1142, 1110, 1095, 1065, 1025, 970, 950, 930, 890, 820, 780, 740, 725, 700, 670, 650, and 623 cm$^{-1}$. $^1$H NMR (CDCl)$\delta$11.76 (1H, brs), 10.62 (1H, brs), 8.34 (1H, d, J=5.2 Hz), 8.08 (1H, d, J=7.9 Hz), 7.85 (1H, d J=5.1 Hz), 7.83 (1H, d, J=7.9 Hz), 7.52 (1H, t, J=7.9 Hz), 7.23 (1H, t, J=7.9 Hz), 6.25 (1H, s), 6.29 (1H, m), 5.57 (2H, m), 5.39 (1H, t, J=9.9 Hz), 4.94 (1H, brs), 4.03 (1H, brs), 3.72 (1H, brd, J=6 Hz), and 3.27 (1H, m). $^{13}$C NMR (CDCl3/D2O)$\delta$144.0, 142.8, 141.7, 141.6, 137.9, 135.5, 133.6, 133.2, 129.7, 128.4, 127.2, 124.0, 121.5, 121.3, 119.6, 114.2, 113.2, 78.4, 71.5, 70.8, 57.5, 53.9, 53.8, 49.6, 47.5, 45.0, 41.5, 39.5, 33.9, 28.8, 26.8, 26.7, 25.3, 24.9, 24.7, and 21.1; UV (MeOH)$\lambda$max 213, 219, 236, 280, 290, 346, 357, mn; HREIMS m/z 548.3510 (C36H44N4O requires 548.3515); EIMS m/z 548 (4), 530 (100), 438 (19), 408 (66), 379 (26), 311 (55), 396 (27), 253 (23), 162 (46), 138 (27), and 98 (32%).

EXAMPLE 2

Preparation of Reduced Derivative

Manzamine A is easily reduced to dihydro-, tetrahydro or hexahydromanzamine A by employing one, two, or three molar equivalents of hydrogen, respectively, in catalytic reduction. A sample of manzamine A and a small amount of catalyst such as Pd/C, Pt/C, or Raney Ni are mixed in a suitable solvent such as ethanol or methanol. The mixture is stirred in the presence of hydrogen in a hydrogenation apparatus. If the reaction is too slow, it would be facilitated by making the media slightly acidic by addition of a trace amount of acid such as HCl. When full reduction to prepare hexahydromanzamine A is desired, the reduction is carried out under elevated pressure of hydrogen using an apparatus such as a Parr hydrogenation apparatus.

EXAMPLE 3

Preparation of Acid Salt

Since manzamine A is a basic compound, its acid salt is easily prepared by mixing manzamine A with an inorganic acid such as HCl, $H_2SO_4$, or an organic acid such as oxalic acid in aqueous ethanol or methanol. As shown by X-ray analysis, manzamine A monohydrochloride has the following structure.

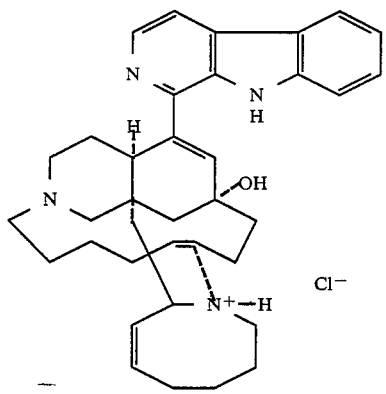

Manzamine A monohydrochloride

ANTITUMOR ACTIVITIES OF THE COMPOUNDS OF THE INVENTION

The following assay method was utilized to illustrate the antitumor effectiveness of the compositions of Formulae I and II corresponding to manzamine A (1) of the example.

P388 MOUSE LEUKEMIA CELL ASSAY

Maintenance of Cell Line

P388 mouse leukemia cells are grown in Dulbecco MEM medium with 10% horse serum, 4 mM glutamine, and 20 ug/ml gentamycin (Biologos, Inc.). Cells are incubated in 10% $CO_2$ and subcultured 2 times per week.

PROCEDURE

1. Add compound to each well of a 24-well plate or tube and allow solvent to evaporate to dryness.
2. Add 2 ml ($1.2 \times 10^5$) cells to each well or tube and mix.
3. Incubate in 10% $CO_2$ at 37° for 48 hours.
4. Read plates with an inverted microscope, scoring activity from 1+ to 4+ as follows: ND (not detectable), >90%; 1+, 75-90%; 2+, 50-74%; 3+, 25-49%; 4+, <25% of control growth. Cell counts are performed on each tube and results are reported as percent of control.

HUMAN TUMOR CELL LINE ASSAY

Maintenance of Cell Line

HCT-8 human colon tumor cells are grown in RPM1 1640 medium (GIBCO). A549 human lung carcinoma cells are cultured in Dulbecco medium (Biologos, Inc.). MDAMB are human breast cancer cells. All media are supplemented with 10% fetal bovine serum and contain 50 ug/ml gentamycin. All human tumor cell lines are incubated at 5% $CO_2$ at 37° subcultured once a week.

PROCEDURE

1. Seed 1 ml cell (5000 HCT-8, 8000 A549, 12000 MDAMB) in each well of a 24-well plate.
2. Incubate in a $CO_2$-incubator for 48 hours.
3. Add compound to each well and incubate for an additional 120 hours.
4. Discard medium and stain with methylene blue (HCT-8) or crystal violet (A549 and MDAMB).
5. Compare cell density of drug-treated well with that of the control (no drug added) as follows: ND (not detechable), >90%; 1+, 75-90%; 2+, 50-74%, 3+, 25-49%, 4+, <25% of control growth.

Positive control—Vinblastine or Vincristine in aqueous solution.

Final Conc. of Vinblastine or Vincristine control (use 2 ul/assay)

| Solution Conc. | Amt added | Final conc. in test |
| --- | --- | --- |
| 5 mg/ml | 2 µl | 5 µg/ml |
| 1 mg/ml | 2 µl | 1 µg/ml |
| 0.1 mg/ml | 2 µl | 0.1 µg/ml |
| 0.05 mg/ml | 2 µl | 0.05 µg/ml |

The results of the above assay are summarized in Table

TABLE 1

| Antitumor Assay Results of Manzamine A | | | | |
| --- | --- | --- | --- | --- |
| Manzamine A Concentration | HCT-8 | A549 | MDAMB | P388 |
| 0.5 µg/ml | 4+ | 4+ | 4+ | — |
| 0.1 µg/ml | ND | ND | ND | — |
| 0.07 µg/ml | — | — | — | $IC_{50}$ |

Table 1 shows that Manzamine A has good antitumor activity at concentrations of at least 0.5 ug/ml against human cancer cells and 0.07 ug/ml against mouse leukemia cells.

It is apparent from the in vitro testing that the compositions of the invention, are effective for inhibiting or destroying tumors and therefore controlling diseases caused by or related to such tumors in hosts such as cancerous cachexia in fulfillment of the objects of the invention.

The scope of the present invention is not limited by the description, examples, and suggested uses herein and modifications can be made without departing from the spirit of the invention. For example, it may be noted that other derivatives of the compositions of examples 1 such as halogenated derivatives may possess antitumor activity analogous to those preferred embodiments described above. Further, the compositions described herein may have other useful applications such as, for example, analgesic applications. Application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A substantially pure compound of the formula:

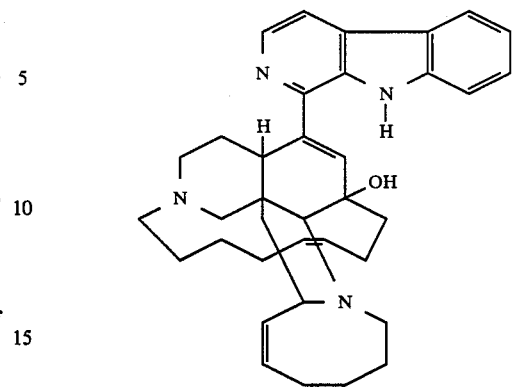

and the dihydro, tetrahydro and hexahydro derivatives thereof.

2. A mineral acid salt of a compound claim 1 wherein the mineral acid is selected from HCl, $H_2SO_4$, $H_3PO_4$ and $HNO_3$.

3. A pharmaceutical composition comprising, as an active ingredient, an amount effective to provide a dosage of between about 0.01 and 100 micrograms of one or more of the compounds of claim 1 and a non-toxic, pharmaceutically acceptable carrier or diluent.

* * * * *

UNITED STATES PATENT AND TRADEMARK OFFICE
CERTIFICATE OF CORRECTION

PATENT NO. : 4,895,854

DATED : January 23, 1990

INVENTOR(S) : Tatsuo Higa, Ryuichi Sakai

It is certified that error appears in the above-identified patent and that said Letters Patent is hereby corrected as shown below:

Column 6: line 37: "metanol" should read --methanol--.

Column 8: line 23: "detechable" should read --detectable--; line 37: "Table" should read --Table 1.--.

Signed and Sealed this

Sixth Day of August, 1991

Attest:

HARRY F. MANBECK, JR.

*Attesting Officer*  *Commissioner of Patents and Trademarks*